US011144825B2

(12) United States Patent
Liu et al.

(10) Patent No.: US 11,144,825 B2
(45) Date of Patent: Oct. 12, 2021

(54) INTERPRETABLE DEEP LEARNING FRAMEWORK FOR MINING AND PREDICTIVE MODELING OF HEALTH CARE DATA

(71) Applicant: University of Southern California, Los Angeles, CA (US)

(72) Inventors: Yan Liu, Los Angeles, CA (US); Zhengping Che, Los Angeles, CA (US); Sanjay Purushotham, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 985 days.

(21) Appl. No.: 15/829,768

(22) Filed: Dec. 1, 2017

(65) Prior Publication Data

US 2018/0158552 A1 Jun. 7, 2018

Related U.S. Application Data

(60) Provisional application No. 62/428,909, filed on Dec. 1, 2016.

(51) Int. Cl.

| | |
|---|---|
| ***G06N 3/08*** | (2006.01) |
| ***G16H 50/20*** | (2018.01) |
| ***G06N 3/04*** | (2006.01) |
| ***G16H 50/70*** | (2018.01) |
| ***G06N 5/02*** | (2006.01) |

(52) U.S. Cl.

CPC ............. *G06N 3/08* (2013.01); *G06N 3/0445* (2013.01); *G06N 3/0454* (2013.01); *G06N 5/025* (2013.01); *G16H 50/20* (2018.01); *G16H 50/70* (2018.01)

(58) Field of Classification Search

CPC ...... G16H 50/20; G16H 50/70; G06N 3/0445; G06N 3/0454; G06N 3/08; G06N 5/025

See application file for complete search history.

(56) References Cited

PUBLICATIONS

Liu, Xuan et al.; Improving the Interpretability of Deep Neural Networks with Knowledge Distillation; 2018 IEEE International Conference on Data Mining Workshops (ICDMW); pp. 905-912. (Year: 2018).*

* cited by examiner

*Primary Examiner* — Stanley K. Hill

(74) *Attorney, Agent, or Firm* — Snell & Wilmer LLP

(57) ABSTRACT

A method for creating an interpretable model for healthcare predictions includes training, by a deep learning processor, a neural network to predict health information by providing training data, including multiple combinations of measured or observed health metrics and corresponding medical results, to the neural network. The method also includes determining, by the deep learning processor and using the neural network, prediction data including predicted results for the measured or observed health metrics for each of the multiple combinations of the measured or observed health metrics based on the training data. The method also includes training, by the deep learning processor or a learning processor, an interpretable machine learning model to make similar predictions as the neural network by providing mimic data, including combinations of the measured or observed health metrics and corresponding predicted results of the prediction data, to the interpretable machine learning model.

9 Claims, 12 Drawing Sheets

300
304
310
308
302
312
312
316
318
y
DEEP LEARNING MODEL
$y_{nn}$
$y_{nn}$
MIMIC MODEL
$y_m$
x
$x_{nn}$
x
306
314
306

900

| METHODS | | MOR (MORTALITY) | | VFD (VENTILATOR FREE DAYS) | |
|---|---|---|---|---|---|
| | | AUROC | AUPRC | AUROC | AUPRC |
| BASELINES | SVM | 0.6437 ± 0.024 | 0.3408 ± 0.034 | 0.7251 ± 0.023 | 0.7901 ± 0.019 |
| | LR | 0.6915 ± 0.027 | 0.3736 ± 0.038 | 0.7592 ± 0.021 | 0.8142 ± 0.019 |
| | DT | 0.6024 ± 0.013 | 0.4369 ± 0.016 | 0.5794 ± 0.022 | 0.7570 ± 0.012 |
| | GBT | 0.7196 ± 0.023 | 0.4171 ± 0.040 | 0.7528 ± 0.017 | 0.8037 ± 0.018 |
| DEEP MODELS | DNN | 0.7266 ± 0.089 | 0.4117 ± 0.122 | 0.7752 ± 0.054 | 0.8341 ± 0.042 |
| | GRU | 0.7666 ± 0.063 | 0.4587 ± 0.104 | 0.7723 ± 0.053 | 0.8131 ± 0.058 |
| | DNN + GRU | 0.7813 ± 0.028 | **0.4874 ± 0.051** | **0.7896 ± 0.019** | **0.8397 ± 0.018** |
| BEST MIMIC MODEL | | **0.7898±0.030** | 0.4766 ± 0.050 | **0.7889 ± 0.018** | 0.8324 ±0.016 |

| TASK | MOR (MORTALITY) | | VFD (VENTILATOR FREE DAYS) | |
|---|---|---|---|---|
| MODEL | GBT | GBTmimic | GBT | GBTmimic |
| FEATURES | PaO2-Day2 (0.0539) | BE-Day0 (0.0433) | MAP-Day1 (0.0423) | MAP-Day1 (0.0384) |
| | MAP-Day1 (0.0510) | δPF-Day1 (0.0431) | PH-Day3 (0.0354) | PIM2S (0.0322) |
| | BE-Day1 (0.0349) | PH-Day1 (0.0386) | MAP-Day2 (0.0297) | VE-Day0 (0.0309) |
| | FiO2-Day3 (0.0341) | PF-Day0 (0.0322) | MAP-Day3 (0.0293) | VI-Day0 (0.0288) |
| | PF-Day0 (0.0324) | MAP-Day1 (0.0309) | PRISM12 (0.0290) | PaO2-Day0 (0.0275) |

FIG. 10

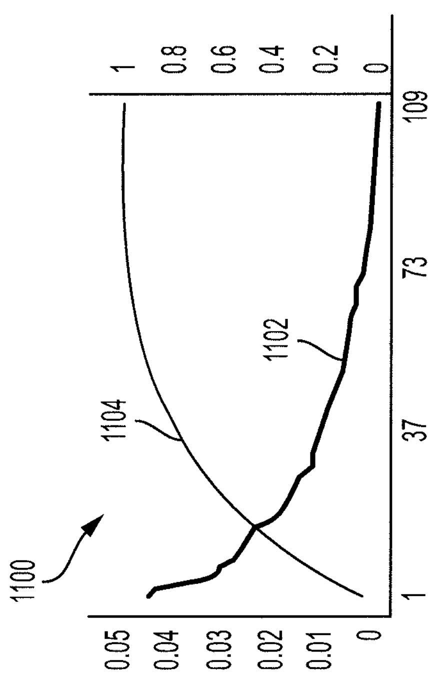
FIG. 11A
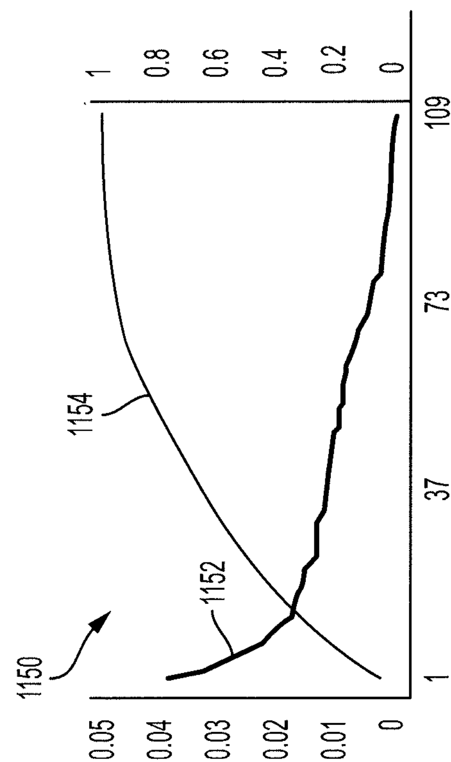
FIG. 11B
1200
STATIC DAY 0 DAY 1 DAY 2 DAY 3
| | STATIC | DAY 0 | DAY 1 | DAY 2 | DAY 3 |
|---|---|---|---|---|---|
| MOR-GBT | 0.136 | 0.172 | 0.285 | 0.185 | 0.221 |
| MOR-GBTmimic | 0.073 | 0.248 | 0.305 | 0.211 | 0.163 |
| VFD-GBT | 0.190 | 0.167 | 0.245 | 0.178 | 0.220 |
| VFD-GBTmimic | 0.276 | 0.189 | 0.202 | 0.171 | 0.163 |
FIG. 12

1400
1402
1404
1406
BE D0
DeltaPF D1
1430
1432
1434
PH D1
1460

INTERPRETABLE DEEP LEARNING FRAMEWORK FOR MINING AND PREDICTIVE MODELING OF HEALTH CARE DATA

CROSS-REFERENCE TO RELATED APPLICATIONS

This application claims the benefit and priority of U.S. Provisional Application No. 62/428,909, entitled "Interpretable Deep Learning Framework for Mining and Predictive Modeling of Health Care Data," filed on Dec. 1, 2016, the entire disclosure of which is hereby incorporated by reference herein in its entirety.

STATEMENT AS TO FEDERALLY SPONSORED RESEARCH

This invention was made with government support under contract numbers IIS1254206 and IIS1134990 awarded by the National Science Foundation (NSF). The government has certain rights in this invention.

BACKGROUND

1. Field

The present disclosure relates to systems and methods for healthcare predictions and, more particularly, to systems and methods for creating interpretable machine learning models that mimic operation of a deep neural network.

2. Description of the Related Art

The national push for electronic health records (EHR) has resulted in an exponential surge in volume, detail, and availability of digital health data. This offers an unprecedented opportunity to infer richer, data-driven descriptions of health and illness. Clinicians are collaborating with computer scientists to improve the state of health care services towards the goal of personalized healthcare. Unlike other data sources, medical/hospital data such as EHR is inherently noisy, irregularly sampled (and/or includes significant missing values), and heterogeneous (meaning that the data may be received from different sources such as lab tests, doctor's notes, monitor readings, and the like). These data properties make it relatively difficult for most existing machine learning models to discover meaningful representations or to make robust predictions. This has resulted in development of novel and sophisticated machine learning solutions. Among these methods, deep learning models (e.g., multilayer neural networks) have achieved state-of-the-art performance on several tasks, such as computational phenotype discovery and predictive modeling.

However, these powerful deep learning models (usually with millions of model parameters) are difficult to interpret. In today's hospitals, model interpretability is not only important but also may be necessary. Thus, clinicians may rely on less powerful but interpretable solutions, such as decision trees, for patient monitoring and decision-making due to the lack of interpretability of neural networks. Decision trees come with disadvantages due to the issues with EHR discussed above. For example, decision trees may easily overfit and perform poorly on large heterogeneous EHR datasets.

Thus, there is a need in the art for systems and methods for training interpretable machine learning models that operate with greater accuracy than current models, such as non-deep learning models (e.g., logistic regression and decision trees) currently in use by clinicians.

SUMMARY

Described herein is a method for creating an interpretable model for healthcare predictions. The method includes training, by a deep learning processor, a neural network to predict health information by providing training data, including multiple combinations of measured or observed health metrics and corresponding medical results, to the neural network. The method also includes determining, by the deep learning processor and using the neural network, prediction data including predicted results for the measured or observed health metrics for each of the multiple combinations of the measured or observed health metrics based on the training data. The method also includes training, by the deep learning processor or a learning processor, an interpretable machine learning model to make similar predictions as the neural network by providing mimic data, including combinations of the measured or observed health metrics and corresponding predicted results of the prediction data, to the interpretable machine learning model. The interpretable machine learning model may be, for example, a gradient boosting tree or other similar machine learning model.

Also described is a method for computational phenotyping. The method includes training a neural network having a prediction layer using an input including at least one of user provided input corresponding to health metrics or sensor input detected by a sensor and corresponding to the health metrics, and using a target corresponding to a desired output for the input. The method also includes determining at least one of soft prediction scores of the prediction layer of the neural network or activations of a highest hidden layer of the neural network corresponding to layer inputs of the highest hidden layer. Activations of the highest hidden layer may include layer outputs of the hidden layer. The method also includes training a gradient boosting tree model to mimic the neural network based on the input to the neural network and the at least one of the soft prediction scores of the prediction layer of the neural network or the activations of the highest hidden layer of the neural network.

Also described is a method for creating an interpretable model for healthcare predictions. The method includes training, by a deep learning processor, a neural network to predict health information by providing training data, including multiple combinations of measured or observed health metrics and corresponding medical results, to the neural network. The method also includes determining, by the deep learning processor and using the neural network, prediction data including learned features of the training data for each of the multiple combinations of the measured or observed health metrics based on the training data. The method also includes training, by the deep learning processor or a learning processor, a classifier to make binary predictions for each of the multiple combinations of the measured or observed health metrics based on the learned features of the training data and the corresponding medical results of the training data. The method also includes training, by the deep learning processor or the learning processor, an interpretable machine learning model to make similar predictions as the neural network by providing classifier data, including combinations of the measured or observed health metrics and corresponding binary predictions, to the interpretable machine learning model.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

FIG. 9 is a table illustrating results of experimental health predictions using a baseline machine learning model, deep neural networks, and an interpretable machine learning model trained to mimic operation of a neural network according to an embodiment of the present invention;

FIG. 10 is a table illustrating top features of an interpretable machine learning model trained to mimic operation of a neural network according to an embodiment of the present invention;

FIGS. 11A and 11B are graphs illustrating individual and cumulative feature importance for mortality prediction (MOR) and ventilator-free days classification (VFD) tasks as determined by an interpretable machine learning model trained to mimic operation of a neural network according to an embodiment of the present invention;

FIG. 12 is a graph illustrating feature importance for static features and temporal features on each day for two tasks as determined by an interpretable machine learning model trained to mimic operation of a neural network according to an embodiment of the present invention;

DETAILED DESCRIPTION

The systems and methods provided herein are designed to provide interpretable machine learning models that mimic operation of neural networks, such as deep neural networks, and are interpretable by humans. A relatively simple yet effective interpretable mimic learning method to distill knowledge from deep networks via Gradient Boosting Trees (GBT) is provided in order to learn interpretable models and strong prediction rules. Preliminary experimental results illustrate that the proposed approach can achieve state-of-the-art prediction performance on a pediatric intensive care unit (ICU) dataset, and can identify features/markers that are important for prediction of mortality and ventilator free days.

Figure 1:
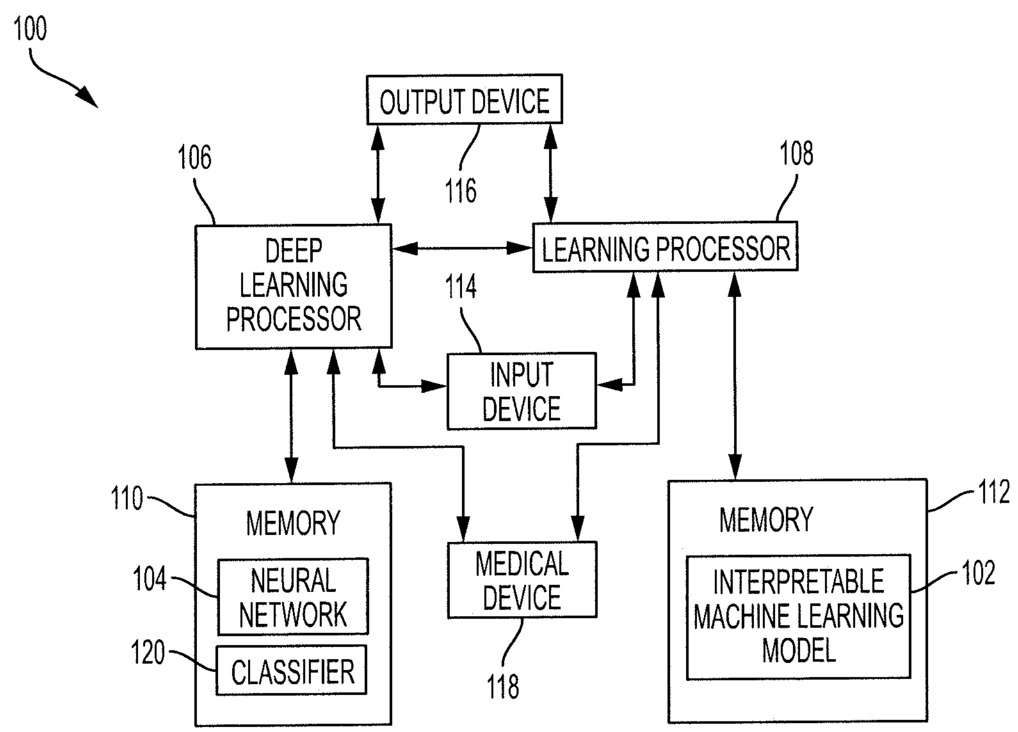
FIG. 1 is a block diagram illustrating a system for creating and training a mimic model, or interpretable machine learning model, to mimic operation of a deep neural network according to an embodiment of the present invention.

Referring to FIG. 1, a system 100 for creating an interpretable machine learning model 102 that mimics operation of a neural network 104 is shown. In particular, the system 100 may include a deep learning processor 106, a learning processor 108, a first memory 110, and a second memory 112. The system 100 may further include an input device 114, an output device 116, and a medical device 118 that may function as an input device.

The input device 114 may include any one or more input device such as a keyboard, a touchscreen, a mouse, a microphone, or the like. The output device 116 may include any one or more output device such as a display, a touchscreen, a speaker, or the like. The medical device 118 may include any medical device capable of outputting detected data such as a cardiac monitor, a pulse sensor, an oxygen sensor, or the like.

In some embodiments, the system 100 may include only the deep learning processor 106 which may perform the functions of the deep learning processor 106 and the learning processor 108. In some embodiments, the system 100 may include only a single memory, which may perform the functions of the memory 110 and the memory 112.

In some embodiments, the deep learning processor 106 and the memory 110 may be located in a first system or device, and the learning processor 108 and the memory 112 may be located in a second system or device. In some embodiments, one or more input device 114 and/or output device 116 may be included in the system 100.

In some embodiments, the deep learning processor 106 may create the neural network 104 (or deep learning model), such as a multilayer feedforward network, a recurrent neural network, a stacked autoencoder network, a long short-term memory network, or any combination thereof.

The deep learning processor 106 may be capable of receiving training data from one or both of the input device 114 and the medical device 118. The training data may include multiple combinations of measured or observed health metrics (such as a temperature, blood pressure, oxygen level, or the like of each of multiple patients) and corresponding medical results (such as a diagnosed disease or whether the patient survived).

The deep learning processor 106 may train the neural network 104 based on the received training data. For example, the deep learning processor 106 may train the neural network 104 to predict results for each of the multiple combinations of measured or observed health metrics. The predicted results may include soft predictions, such as one or more predicted results, and a corresponding likelihood of each being correct. For example, a soft prediction may include a value between 0 and 1 that indicates likelihood of patient survival, with a 1 being a prediction with 100 percent (100%) accuracy that the patient will die, and a 0.5 corresponding to a 50% likelihood that the patient will die.

The predicted results may be created in what is referred to as a prediction layer. The deep learning processor 106 may likewise train a neural network 104 to learn features of the training data. The learned features may be referred to as activations and may be learned or created in a hidden layer of the neural network 104. The learned features may indicate how the neural network 104 made the prediction. The learned features may be relatively difficult for a human to interpret and, thus, may render the neural network 104 impractical for use in a clinical setting. The deep learning processor 106 may make the predictions based on applying the learned features to each of the multiple combinations of measured or observed health metrics.

In some embodiments, the deep learning processor 106 may also train and/or create a classifier 120. The classifier 120 may be trained to mimic operation of the neural network 104. The classifier 120 may be trained based on the learned features from the neural network 104 and the corresponding medical results of the training data. In some embodiments, the classifier 120 may output a binary prediction, such as a yes or no answer to a question.

The memory 110 may store data usable by the deep learning processor 106. For example, the memory 110 may store the neural network 104 along with the classifier 120.

One or both of the learning processor 108 or the deep learning processor 106 may train and/or create the interpretable machine learning model 102. The interpretable machine learning model 102 may be trained to mimic the health prediction operations of the neural network 104, and may thus be referred to as a "mimic model" 102. The interpretable machine learning model 102 may be less complex than the neural network 104, and operation thereof may be relatively easy to interpret by humans. For example, the interpretable machine learning model 102 may include a linear support vector machine model, a logistic regression model, a linear regression model, a decision tree model, a gradient boosting tree model, a shallow neural network, or the like.

In some embodiments, the interpretable machine learning model 102 may be trained using the predicted results from the neural network 104 along with the corresponding combinations of measured or observed health metrics. For example, the interpretable machine learning model 102 may be provided with each set of the measured or observed health metrics and the corresponding prediction from the neural network 104. In some embodiments, the interpretable machine learning model 102 may be trained using the binary prediction from the classifier 120 along with the corresponding combinations of measured or observed health metrics.

The interpretable machine learning model 102 may be trained to output soft predictions that mimic the predictions of the neural network 104 based on the same measured or observed health metrics. In that regard, the learning processor 108 may receive a new set of measured or observed health metrics and may predict a predicted health result (i.e., a soft prediction) based on the new set of measured or observed health metrics. The prediction by the learning processor 108 that is based on the interpretable machine learning model 102 may include one or more predicted result along with a likelihood of accuracy of the prediction.

The memory 112 may be designed to store data usable by the learning processor 108. For example, the memory 112 may store the interpretable machine learning model 102.

After creation or training of the interpretable machine learning model 102, the learning processor 108 may control the output device 116 to output the interpretable machine learning model 102 in a format that is viewable and interpretable by humans. In some embodiments, the learning processor 108 may control the output device 116 to output the predicted results that are predicted by the interpretable machine learning model 102.

Figure 2:
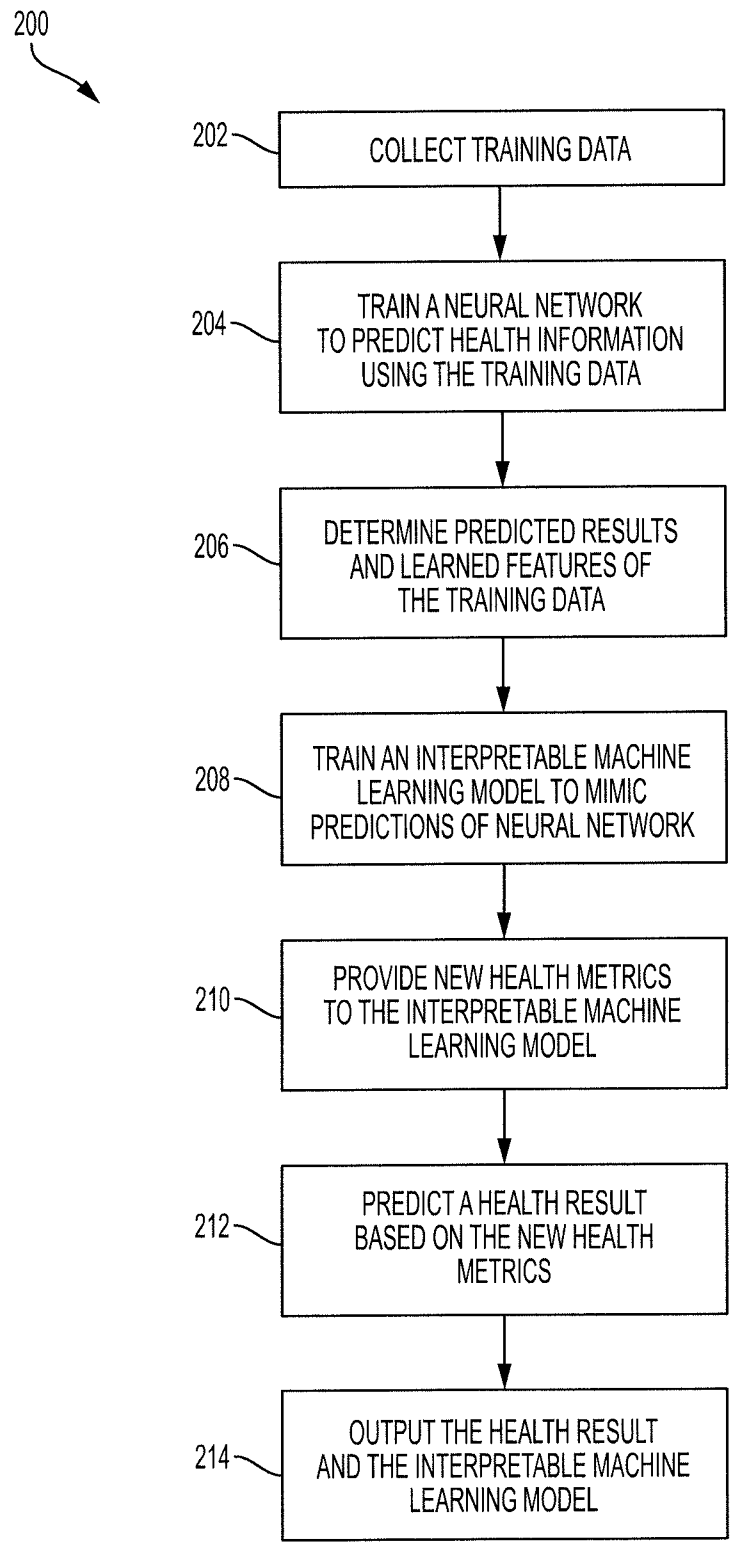
FIG. 2 is a flowchart illustrating a method for creating and training an interpretable machine learning model to mimic operation of a neural network according to an embodiment of the present invention.

Turning to FIG. 2, a method 200 for creating and training an interpretable model for healthcare predictions is shown. The method 200 may be created by a system similar to the system 100 of FIG. 1.

In block 202, training data may be collected. For example, the training data may be received via an input device or via a medical device. The training data may include electronic health record (EHR) data. The training data may include multiple sets of measured or observed health metrics and corresponding medical results.

In block 204, a deep learning processor may train a neural network (or other deep learning model) to predict health information based on the training data. For example, the neural network may be trained to predict a health outcome of a patient based on a set of measured or observed health metrics of the patient. The neural network may make relatively accurate health predictions, which may be of greater accuracy than an interpretable machine learning model that is trained using the same training data. However, the reasoning or logic used by the neural network to make the prediction may be relatively difficult or impossible for a human to understand. In that regard, it is desirable to create an interpretable machine learning model, or mimic model, that can predict health results with a similar accuracy as the neural network while basing the predictions on logic that can be relatively easily understood by humans.

In block 206, the deep learning processor may determine or predict predicted results for each set of measured or observed health metrics of the training data. The deep learning processor may also determine learned features of the training data. The learned features may include, for example, activations of a hidden layer of the neural network. The deep learning processor may use the learned features to predict health results for sets of measured or observed health metrics. Stated differently, the learned features include at least some of the logic used by the neural network to make the predictions. These learned features may be relatively difficult for a human to understand.

In block 208, the deep learning processor or a learning processor may train an interpretable machine learning model, such as a gradient boosting tree or any other interpretable machine learning model, to mimic predictions of the neural network. For example, the interpretable machine learning model may be provided with the multiple combinations of measured or observed health metrics that were included in the training data collected in block 202, and may also be provided with the predicted results from the neural network that were determined in blocked 206.

After training in this manner, the interpretable machine learning model, or mimic model, may make predictions with relatively the same accuracy as the original neural network.

However, the mimic model provides the advantage of being relatively easy to interpret by humans, which allows humans to understand the important features used in making the prediction. This is relatively important because it helps clinicians not only make predictions for patients but also understand the reasoning behind the prediction. The clinicians may also learn new ways to identify and treat disease using the newly-available reasoning provided using the mimic framework provided herein.

In some embodiments, a gradient boosting tree may provide an ideal combination of relatively accurate predictions along with relative ease of interpretation by humans. Therefore, a gradient boosting tree may be selected as the interpretable machine learning model.

In block 210, a new set of measured or observed health metrics may be provided to the interpretable machine learning model, such as via an input device (which may include a medical device). The new set of measured or observed health metrics may correspond to a current patient. For example, the patient may be located in a health clinic and the health metrics may be detected or measured by a clinician (or a medical device) and provided as input to the learning processor. The health metrics may include, for example, a patient temperature, heart rate, oxygen level, breathing rate, blood ph level, or the like.

In block 212, the learning processor may predict a health result of the patient based on the new set of measured or observed health metrics using the interpretable machine learning model. The predicted health results may mimic a result that would be predicted by the neural network. In that regard, the predicted health result may have relatively the same accuracy as one predicted by the neural network.

In block 214, the learning processor may control an output device to output the predicted health result of the patient. A clinician (i.e., a doctor or other qualified medical professional) may view the predicted health result and may develop a treatment plan for the patient based on the predicted health result. The predicted health result may be a soft prediction, meaning that it includes a prediction and a corresponding likelihood of the prediction being accurate. Soft predictions may be more valuable to clinicians than hard predictions (binary output) due to the additional information included in the soft predictions (i.e., the likelihood of the prediction being accurate).

In some embodiments, the learning processor may also output the interpretable machine learning model. For example, if the interpretable machine learning model is a gradient boosting tree model then the learning processor may output the various decision trees and weights of the gradient boosting tree mimic model. The clinician may be able to identify the reasoning or logic behind the prediction based on the mimic model and may further develop the treatment plan based on the mimic model. The reasoning or logic behind the prediction may provide valuable information to the clinician. For example, if the prediction includes that the patient has a high likelihood of mortality and a major factor is the breathing rate of the patient, then the clinician may place the patient on a ventilator to increase the chance of survival.

Figure 3:
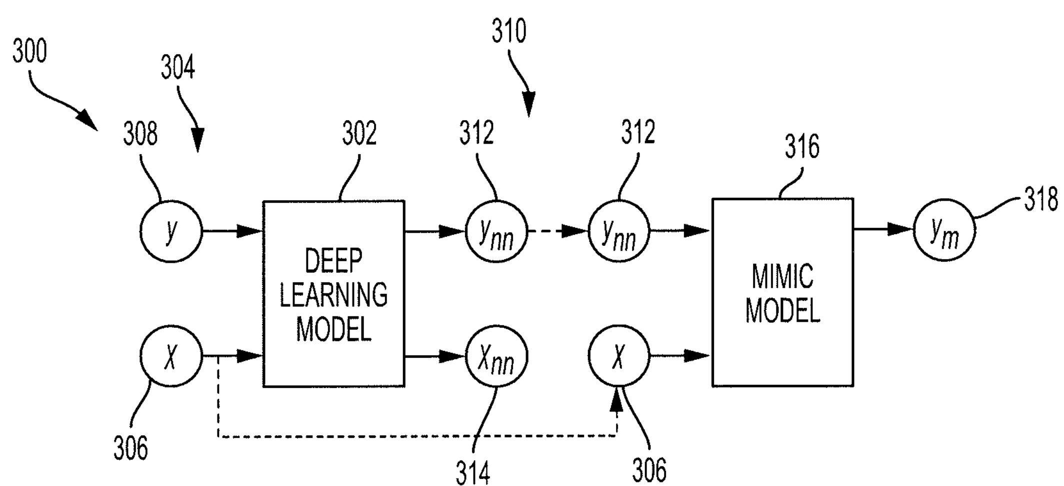
FIG. 3 is a block diagram illustrating a system for creating and training an interpretable machine learning model to mimic operation of a neural network according to an embodiment of the present invention.

Referring now to FIG. 3, a system 300 may be used to create an interpretable model for healthcare predictions. For example, the system 300 may create the interpretable model using a method similar to the method 200 of FIG. 2. In particular, a deep learning model 302, such as a neural network, may receive training data 304. The training data 304 may include multiple combinations of measured or observed health metrics 306 and corresponding medical results 308.

The deep learning model 302 may determine prediction data 310 that includes predicted results 312 for each of the measured or observed health metrics 306 along with learned features 314.

A mimic model 316 may be an interpretable machine learning model. The mimic model 316 may receive the predicted results 312 along with the multiple combinations of measured or observed health metrics 306. The mimic model 316 may be trained to mimic operation of the deep learning model 302 based on the combinations of measured or observed health metrics 306 and the corresponding predicted results that correspond to each of the combinations of health metrics. In that regard, the mimic model 316 may be designed to output predictions 318 that mimic the predicted results 312 of the deep learning model 302.

Figure 4:
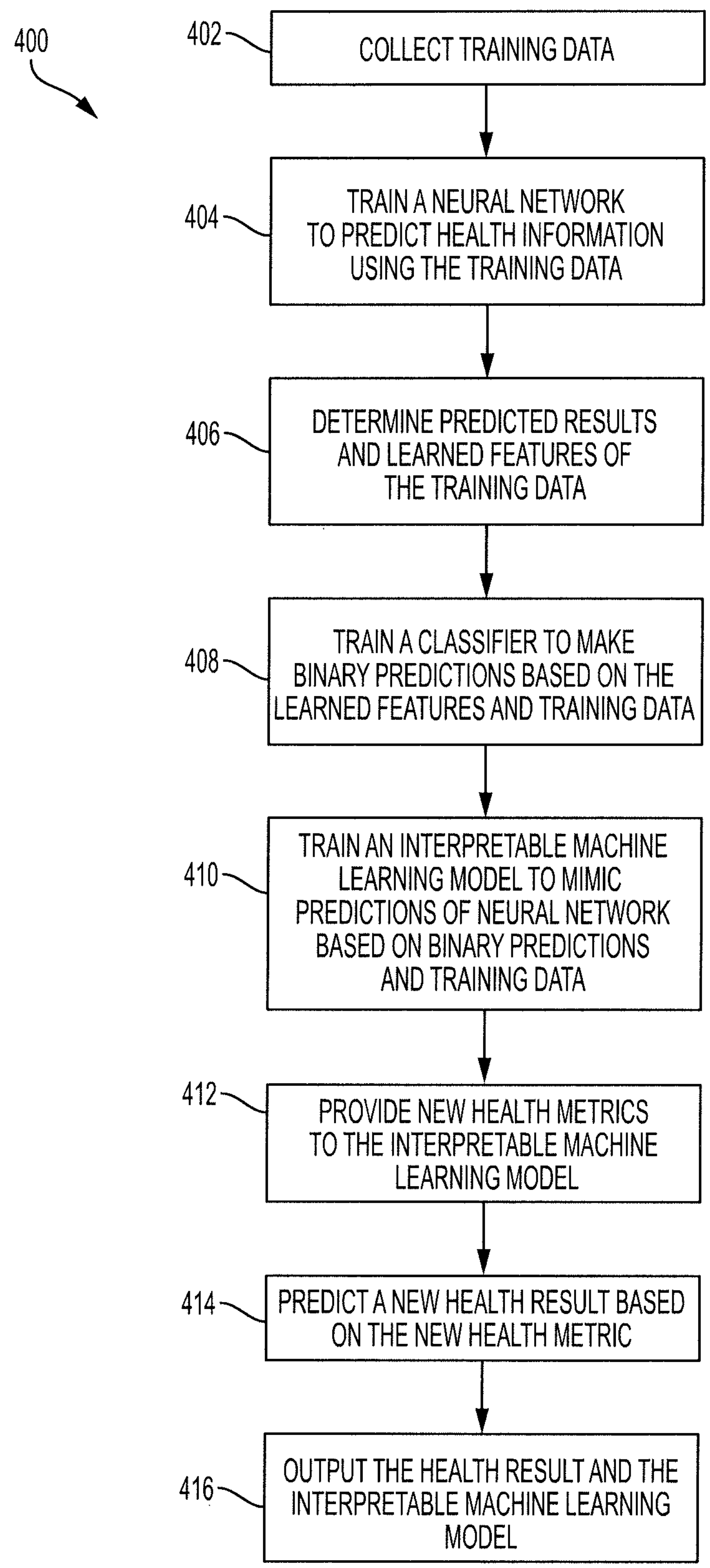
FIG. 4 is a flowchart illustrating a method for creating and training an interpretable machine learning model to mimic operation of a neural network according to an embodiment of the present invention.

Turning now to FIG. 4, a method 400 for creating an interpretable model for healthcare predictions is shown. In block 402, a deep learning processor may receive or collect training data in a manner similar to that of block 202 of FIG. 2. In block 404, the deep learning processor may train a neural network using the training data in a similar manner as in block 204 of FIG. 2. In block 406, the deep learning processor may determine predicted results and learned features of the training data in a similar manner as in block 206 of FIG. 2.

In block 408, the deep learning processor or a learning processor may train a classifier to make binary predictions based on measured or observed health metrics. The predictions made by the classifier may include binary predictions, such as a yes or no answer to a question. The classifier may make binary predictions for each of the combinations of measured or observed health metrics of the training data.

Training the classifier in block 408 may be performed differently than training the interpretable machine learning model in block 208 of FIG. 2. In particular, the classifier may be trained using the learned features determined by the neural network in block 406 and using the corresponding medical results of the training data. In that regard, a classifier may be trained to make binary health predictions that are similar to the predictions made by the neural network. However, the predictions made by the classifier may be binary, as opposed to the more desirable soft predictions of the neural network.

In that regard and in block 410, the deep learning processor or the learning processor may train an interpretable machine learning model to mimic predictions of the neural network. In particular, the processor may train the interpretable machine learning model using each combination of the measured or observed health metrics of the training data along with the binary predictions for each combination. The interpretable machine learning model may make similar soft predictions as the neural network. In that regard, the interpretable machine learning model trained in block 410 may operate in a similar manner as the interpretable machine learning model trained in block 208 of FIG. 2. In that regard, the interpretable machine learning model may be a mimic model and may make soft predictions that are similar in accuracy as the neural network.

In block 412, new health metrics may be provided to the interpretable machine learning model. The new health metrics may correspond to data measured or collected from a new patient. In that regard, block 412 may be performed in a similar manner as block 210 of FIG. 2.

In block 414, the learning processor may predict a new health result based on the new health metrics in a similar manner as performed in block 212 of FIG. 2.

In block 416, the learning processor may control an output device to output one or both of the new health result along with the interpretable machine learning model. This may be performed in a similar manner as block 214 of FIG. 2. In some embodiments, the learning processor may also control the output device to output the classifier that was trained in block 408.

Figure 5:
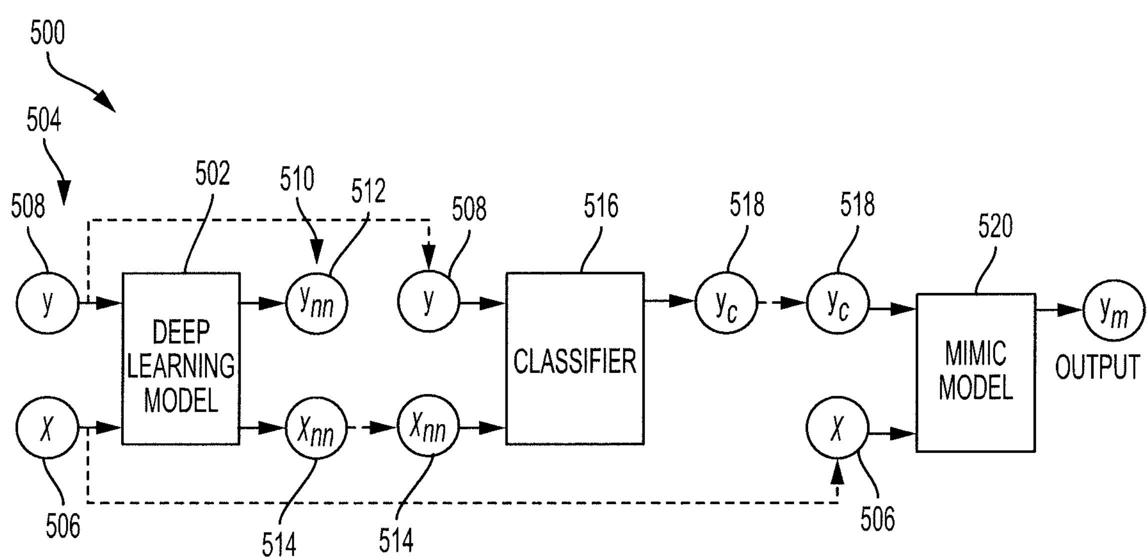
FIG. 5 is a block diagram illustrating a system for creating and training an interpretable machine learning model to mimic operation of a neural network according to an embodiment of the present invention.

Turning to FIG. 5, a system 500 may be used to create an interpretable machine learning model for predicting health results. The system may create the interpretable machine learning model using a method similar to the method 400 of FIG. 4.

The system 500 may include a deep learning model 502 such as a neural network, that may receive training data 504. The training data 504 may include multiple combinations of measured or observed health metrics 506 along with corresponding medical results 508.

The deep learning model 502 may determine prediction data 510 that includes predicted results 512 for each of the measured or observed health metrics 506, along with learned features 514.

A classifier 516 may receive the medical results 508 and the corresponding learned features 514. The classifier 516 may determine binary predicted results 518 for each of the measured or observed health metrics 506 based on the medical results 508 and the corresponding learned features 514.

A mimic model 520 may be an interpretable machine learning model. The mimic model 520 may receive the measured or observed health metrics 506 along with the binary predicted results 518 for each of the measured or observed health metrics 506. The mimic model 520 may be trained to mimic predictions of the deep learning model 502 based on the binary predicted results 518 and the corresponding measured or observed health metrics 506. The mimic model 520 may be trained to output predictions that mimic those of the deep learning model 502 (i.e., the mimic model 520 may output soft predictions that have a similar accuracy as the prediction 510 of the deep learning model 502).

A multilayer feedforward network (DNN) may be used as a neural network as described herein, and may include multiple nonlinear layers (which may be hidden layers) and possibly one prediction layer on the top to solve a classification task. The first layer takes the concatenation of static and flattened temporal variables as the input (X), and the output from each layer is used as the input to the next layer. The transformation of each layer can be shown by Equation 1 below:

$$X^{l+1}=f^l(x^l)=s^l(W^lX^l+b^l) \quad \text{Equation 1:}$$

Figure 6:
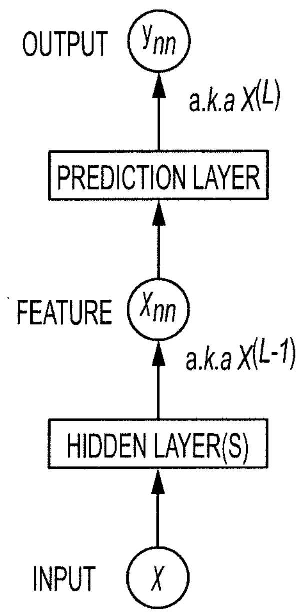
FIG. 6 is a block diagram illustrating an exemplary feedforward neural network (DNN) according to an embodiment of the present invention.

In Equation 1, $W^l$ and $b^l$ represent, respectively, the weight matrix and bias vector of layer l, and $s^l$ is a nonlinear activation function, which usually takes one of logistic sigmoid, tan h, or ReLU. A feed-forward network with L layers is shown in FIG. 6, the output of the top-most layer $y_{nn}=X^L$ is the prediction score, which lies in [0, 1] (i.e., may be a soft prediction). The output of second top layer $X^{L-1}$ may be treated as the features extracted by DNN, and these features may be helpful as inputs for other prediction models. During training, the cross-entropy prediction loss between the prediction output and the true label may be optimized.

Figure 7A:
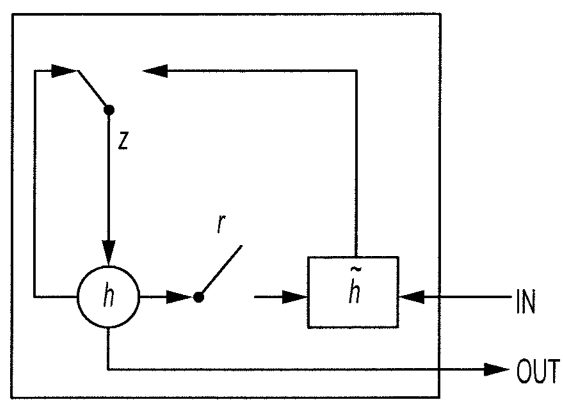
FIGS. 7A and 7B are block diagrams illustrating an exemplary recurrent neural network (RNN) with a gated recurrent unit (GRU) according to an embodiment of the present invention.

A Recurrent neural network (RNN) model, such as Long Short-Term Memory (LSTM) and Gated Recurrent Unit (GRU), may also or instead be used as a neural network as described herein, and have been shown to be successful at handling complex sequence inputs and capturing long term dependencies. In various experiments, GRU was used to model temporal modalities since it has a relatively simple architecture compared to classical LSTM and has been shown to achieve state-of-the-art performance relative to all RNN models for modeling sequential data. FIG. 7A illustrates exemplary structure of a GRU. $x_t \in R^P$ denotes variables at time t, where $1 \le t \le T$. At each time t, GRU has a reset gate $r_t^j$ and an update gate $z_t^j$ for each of the hidden states $h_t^j$. The update function may be shown by equations 2-5 below.

$$z_t=\sigma(W_zx_t+U_zh_{t-1}+b_z) \quad \text{Equation 2:}$$

$$\tilde{h}_t=\tan h(Wx_t+U(r_t \odot h_{t-1})+b) \quad \text{Equation 3:}$$

$$r_t=\sigma(W_rx_t+U_rh_{t-1}+b_r) \quad \text{Equation 4:}$$

$$h_t=(1-z_t)\odot h_{t-1}+z_t\odot \tilde{h}_t \quad \text{Equation 5:}$$

Figure 7B:
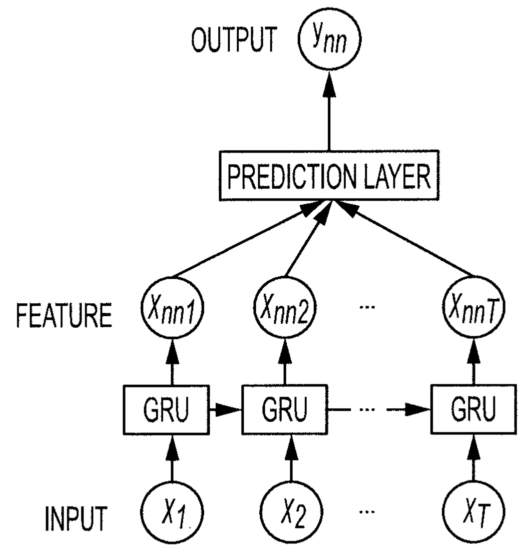

In Equations 2-5, $W_z$, $W_r$, W, $U_z$, $U_r$, U, and vectors $b_z$, $b_r$, and b are model parameters. At time t, the hidden states $h_t$ are treated as the output of GRU $x_{nnt}$ at that time. FIG. 7B illustrates a GRU prediction model. As shown in FIG. 7B, the output of the GRU is flattened at each time step, and another sigmoid layer is added on top to obtain the prediction $y_{nn}$.

A combination of DNN and GRU may also be used as a neural network as described herein. One limitation of GRU is that it only aims to model temporal data, while usually both static and temporal features are available in EHR data from health clinics, such as intensive care units (ICUs). Therefore, a combination model of feed-forward network (DNN) and GRU may be advantageous in such settings.

Figure 8:
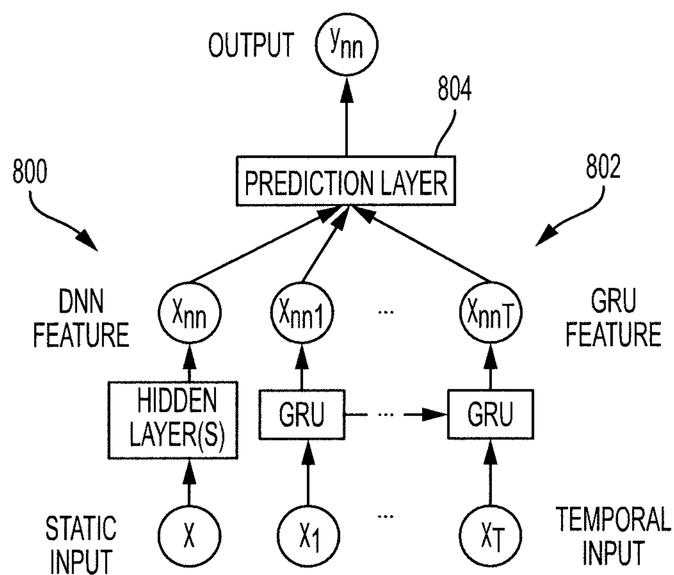
FIG. 8 is a block diagram illustrating an exemplary combination of a feedforward neural network and a recurrent neural network according to an embodiment of the present invention.

A combined DNN and GRU model is shown in FIG. 8. As shown in the combination model, one DNN model 800 is used to take static input features, and one GRU model 802 is used to take temporal input features. A shared layer 804 may be added on top, which takes the features from both GRU and DNN to make a prediction, and all of the parts may be trained jointly.

A general concept of knowledge distillation is to train a relatively large, slow, and accurate model and transfer its knowledge to a relatively smaller and faster, yet still accurate, model. This concept is shown as the methods 200 and 400 of FIGS. 2 and 4, respectively, and may be referred to as mimic learning. In particular, mimic learning uses a complex model (such as a deep neural network, or an ensemble of network models) as a teacher/base model to train a student/mimic model (such as a shallow neural network or a single network model). The manner of distilling the knowledge to the mimic model is to utilize soft labels learned from the teacher/base (i.e., deep neural network) model as target labels while training the student/mimic model. The soft labels (i.e., the predicted results or soft predictions), in contrast to the hard labels (i.e., the corresponding medical results, which are typically binary) from the raw data, may provide the greatest value from the teacher model, as the values typically can range anywhere from 0 to 1 (i.e., may have any value between 0 and 1, rather than being binary).

Conventional shallow neural networks are less accurate than deep neural networks, if trained using the same training data. However, by providing the soft labels to the shallow neural network, the shallow model (i.e., the interpretable machine learning model) is capable of learning the knowledge extracted by the deep neural network and can achieve similar or better performance than the deep neural network.

Various reasons exist which may explain why the interpretable machine learning model can achieve similar or better performance than the deep neural network. For example, potential noise and error in the training data (such as input features or labels) may affect the training efficacy of the relatively simple models. The teacher model may eliminate some of this noise, thus making the learning easier for the student model. Soft labels (i.e., the predicted results) typically are more informative than the original hard label, such that using the soft labels may provide improved performance by the student model. Additionally, the mimic approach may be treated as an implicit manner of regularization on the teacher model, which may result in the student (i.e., mimic) model being more robust and less likely to overfit.

The parameters of the student model may be estimated by minimizing the squared loss between the soft labels from the teacher label and the predictions by the student model. That is, given a set of data $\{X_i\}$ where i=1, 2, . . . N, as well as the soft label $y_{s,i}$ from the teacher model, the student model F(X) may be estimated by minimizing $\Sigma_{i=1}^{N}\|y_{s,i}-f(X_i)\|^2$.

As mentioned above, gradient boosting trees (GBT) may provide an ideal interpretable machine learning (i.e., mimic) model as it provides a desirable mix of learning capacity and interpretability. A gradient boosting tree is a method that trains an ensemble of weak learners to optimize a differentiable loss function by stages. The basic idea is that the prediction function F(X) can be approximated by a linear combination of several functions (under some assumptions), and these functions can be sought using gradient descent approaches.

Gradient Boosting Trees (GBT) takes a simple classification or regression tree as weak learner, and add one weak learner to the entire model per stage. At an $M^{th}$ stage, the current model may be $F_m(X)$, then the Gradient Boosting method may attempt to find a weak model $h_m(X)$ to fit the gradient of the loss function with respect to F(X) at $F_m(X)$. The coefficient $\gamma_m$ of the stage function is computed using a line search strategy to minimize the loss. To keep gradient boosting from overfitting, a regularization method called shrinkage may be employed, which multiplies a small learning rate v to the stage function in each stage. The final model with M stages can be written as shown in Equation 6 below.

$$F_M(X)=\Sigma_{i=1}^{M} v\gamma_i h_i(X)+\text{const} \quad \text{Equation 6:}$$

Two general training pipelines within the interpretable mimic learning framework are described above (i.e., the method 200 of FIG. 2 and the method 400 of FIG. 4), which utilize the learned feature representations or the soft labels from deep learning models to train or assist the student model. The main difference between these two pipelines is whether to take the soft labels directly from the deep learning models or from a helper classifier trained using the features from the deep neural networks.

In pipeline 1 (FIGS. 2 and 3), predicted soft labels are used directly from deep learning models. In the first step, a deep learning model is trained, which can be a simple feedforward network or GRU, given the input X and the original target y (which is either 0 or 1 for binary classification). Then, for each input sample X, we obtain the soft prediction score $y_{nn} \in [0, 1]$ from the prediction layer of the neural network. Usually, the learned soft score $y_{nn}$ is relatively close, but not exactly the same as, the original binary label y. In a second step, a mimic Gradient boosting model is trained, given the raw input X and the soft label $y_{nn}$ as the model input and target, respectively. We train the mimic model to minimize the mean squared error of the output $y_m$ to the soft label $y_{nn}$.

In Pipeline 2 (FIGS. 4 and 5), the learned features from deep learning models are taken instead of the prediction scores, provided to a helper classifier, and mimic the performance based on the prediction scores from the helper classifier. For each input sample X, the activations $X_{nn}$ of the highest hidden layer are obtained, which can be $X^{(L-1)}$ from an L-layer feedforward network, or the flattened output at all time steps from GRU. These obtained activations may be considered as the extracted representations from the neural network, and its dimension may be changed by varying the size of the neural networks. $X_{nn}$ may then be provided to a helper classifier (e.g., logistic regression or support vector machines), to predict the original task y, and the soft prediction score $y_c$ may be taken from the classifier. Finally, a mimic Gradient boosting model may be trained given X and $y_c$.

In both pipelines, the mimic model trained in the last step is applied to predict the labels of testing examples.

The interpretable mimic learning approach described herein provides several advantages. First, the approach can provide models with state-of-the-art prediction performance. The teacher deep learning model outperforms the traditional methods, and student gradient boosting tree model maintains the performance of the teacher model by mimicking its predictions. Second, the approach yields a model with greater interpretability than the original deep learning model, which is complex to interpret due to its complex network structures and the large quantity of parameters.

The student gradient boosting tree model has greater interpretability than the original deep model since each feature's impact on prediction can be studied, and simple decision rules may be obtained from the tree structures. Furthermore, the mimic learning approach uses the soft targets from the teacher deep learning model to avoid overfitting to the original data. Thus, the student model may provide greater generalizations than standard decision tree methods or other models, which tend to overfit to original data.

Experiments were conducted on a pediatric ICU dataset to answer the following questions: (a) how does the mimic learning framework perform when compared to the state-of-the-art deep learning methods and other machine learning methods; and (b) how are the models learned through the proposed mimic learning framework interpreted? The dataset, methods, empirical results, and interpretations are examined below to answer the above questions.

The experiments on the pediatric ICU dataset were collected at the Children's Hospital Los Angeles. This dataset consists of health records from 398 patients with acute lung injury in the pediatric ICU at Children's Hospital Los Angeles. It contains a set of 27 static features such as demographic information and admission diagnoses, and another set of 21 temporal features (recorded daily) such as monitoring features and discretized scores made by experts, for the initial four days of mechanical ventilation. Simple imputation was applied to fill in missing values, where the majority value for binary variables are taken, and an empirical mean for other variables. This choice of imputation may not be the optimal one and finding better imputation methods is another important research direction beyond the scope of this disclosure. For fair comparison, the same imputed data was used for evaluation of all the methods.

Two binary classification (prediction) tasks were performed on this dataset. The first is mortality (MOR): the aim is to predict whether the patient dies within 60 days after admission. 20.10% of all the patients are mortality positive (i.e., patients died). The second is a quantity of ventilator free days (VFD): the aim is to evaluate a surrogate outcome of morbidity and mortality (ventilator free days, of which lower value is undesirable), by identifying patients who survive and are on a ventilator for longer than 14 days within 28 days after admission. Since here lower VFD is undesirable, it is an undesirable outcome if the value ≤14, otherwise it is a desirable outcome. 59.05% of all the patients have VFD >14.

The methods used in the experiments were classified into the following groups:

Baseline machine learning methods, which are popular in healthcare domains and include Linear Support Vector Machine (SVM), Logistic Regression (LR), Decision Trees (DT) and Gradient Boosting Trees (GBT).

Deep network models, which include feed-forward neural network (DNN), recurrent neural network with Gated Recurrent Units GRU, and combinations of the two (DNN+GRU).

Proposed mimic learning models: for each of the deep models shown above, both of the mimic learning pipelines are used and evaluated.

All of the baseline methods were trained with the same input, i.e., the concatenation of the static and flattened temporal features. The DNN implementations have two hidden layers and one prediction layer. The size of each hidden layer is set to be twice as large as the input size. For GRU, only the temporal features are used as input. The size of the other models are set to have a similar same scale.

Several strategies are applied to avoid overfitting and to train robust deep learning models. In particular, the experiments train for 250 epochs with early stopping criterion based on the loss on validation dataset. Stochastic gradient descent (SGD) is used for DNN, and Adam with gradient clipping is used for other deep learning models. Weight regularizers and dropout are also used for deep learning models. Similarly, for Gradient Boosting methods, the maximum number of boosting stages is set to 100, with early stopping based on the Area Under Receiver Operating Characteristic (AUROC) score on validation dataset. All baseline methods are implemented using the scikit-learn package and all deep networks in the Theano and Keras platforms.

FIG. 9 illustrates a table 900 that shows the prediction performance (area under receiver operating characteristic curve (AUROC) and area under precision-recall curve (AUPRC)) of all the methods described above. The results are averaged over 5 random trials of 5-fold cross validation. It is observed that for both tasks, all deep learning models perform better than baseline models. The optimal performance by deep learning models is achieved by the combination model, which use both DNN and GRU to handle static and temporal input variables, respectively. The interpretable mimic approach (i.e., the mimic models) achieves similar (or even slightly better performance) as the deep models. It was found that pipeline 1 (FIGS. 2 and 3) yields slightly better performance than pipeline 2 (FIGS. 4 and 5). For example, pipeline 1 and pipeline 2 obtain AUROC score of 0.7898 and 0.7670 for MOR task, and 0.7889 and 0.7799 for VFD task, respectively. Therefore, the pipeline 1 model (i.e., the method illustrated in FIG. 2) is used in the below discussion and may be preferred over pipeline 2.

Next, a series of solutions are discussed to interpret Gradient Boosting trees in the mimic models, including feature importance measure, partial dependence plots and important decision rules.

A common interpretation tool for tree-based algorithms is feature importance (influence of specific variables). The influence of one variable j in a single tree T with L splits is based on a quantity of times when the variable is selected to split the data samples. Formally, the influence InF is defined as shown in Equation 7 below:

$$Inf_j(T)=\Sigma_{l=1}^{L-1} l_i^2 \mathrm{I}(S_1=j) \qquad \text{Equation 7:}$$

In Equation 7, $l_i^2$ refers to the empirical squared improvement after split l, and I is the identity function. The importance score of GBT is defined as the average influence across all trees and normalized across all variables. Although importance score is not about how the feature is actually used in the model, it proves to be a useful metric for feature selection.

FIG. 10 illustrates a table 1000 showing the most useful features for MOR and VFD tasks, respectively, from both GBT and optimal GBT mimic models. It was found that some important features are shared by several models, e.g., MAP (Mean Airway Pressure) at day 1, δPF (Change of PaO2/FIO2 Ratio) at day 1, etc. Most of the top features may be temporal features. Among the static features, PRISM (Pediatric Risk of Mortality) score, which is developed and commonly used by doctors and medical experts, may be the most useful static variable. As the mimic method significantly outperforms the original GBT method, it is worthwhile to investigate which features are considered as more important or less important by the mimic method.

FIGS. 11A and 11B are plots 1100, 1150 illustrating individual importance 1102, 1152 (i.e., feature importance of a single feature) and cumulative importance 1104, 1154 (i.e., aggregated importance of features sorted by importance score) of the two tasks. From this figure, it can be observed that no dominant feature (i.e., a feature with high importance score among all features) exists, and the most dominant feature has an importance score less than 0.05, which implies that more features are needed for obtaining better predictions. It is also noticed that for the MOR task (FIG. 11A), fewer features are required relative to the VFD task (FIG. 11B) based on the cumulative feature importance scores (quantity of features when the cumulative score >0.8 is 41 for MOR and 52 for VFD).

FIG. 12 is a graph illustrating aggregated feature importance scores on different days. The trend of feature importance for GBT mimic methods is Day 1>Day 0>Day 2>Day 3, which means early observations may be of greater use for both MOR and VFD prediction tasks. On the other hand, for GBT methods, the trend is Day 1>Day 3>Day 2>Day 0 for both the tasks. Overall, Day-1 features may be the most useful across all the tasks and models.

Visualizations may provide greater interpretability of the mimic models trained in the experiment. GBT mimic may be visualized by plotting the partial dependence of a specific variable or a subset of variables. The partial dependence can be treated as the approximation of the prediction function given only a set of specific variable(s). It may be obtained by calculating the prediction value by marginalizing over the values of all other variables.

Figure 13:
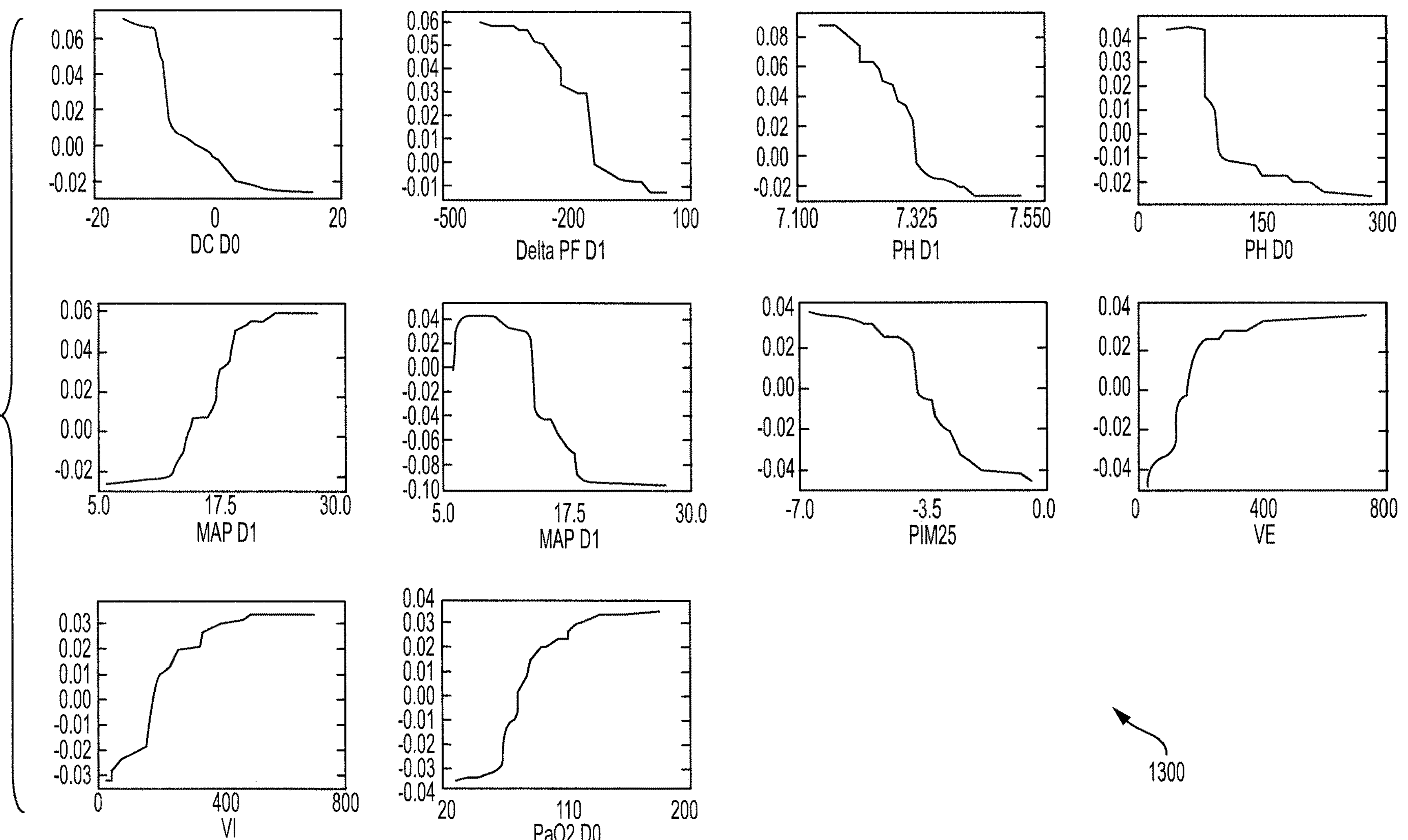
FIG. 13 illustrates multiple partial dependence plots of top features of an interpretable machine learning model trained to mimic operation of a neural network according to an embodiment of the present invention.

One-Way Partial Dependence: FIG. 10 illustrates a list of relatively important features selected by the mimic model (GBT mimic) and GBT. It is of interest to study how these features influence the model predictions. Furthermore, different mimic models may be compared by investigating the influence of the same variable in different models. FIG. 13 illustrates multiple plots 1300 illustrating one-way partial dependence scores from GBT mimic for the two tasks. The results are relatively easy to interpret and may match existing findings. For instance, the mimic model predicts a higher chance of mortality when the patient has value of PH-Day0 below 7.325. This conforms to the existing knowledge that human blood (in healthy people) stays in a relatively narrow pH range (i.e., such as between 7.35-7.45). Base blood pH may be low due to metabolic acidosis (more negative values for base excess), or due to high carbon dioxide levels (ineffective ventilation). The findings that pH and Base excess are associated with higher mortality corroborate clinical knowledge. More useful rules from the mimic models may be found via the partial dependence plots, which provide deeper insights into the results of the deep models.

Figure 14:
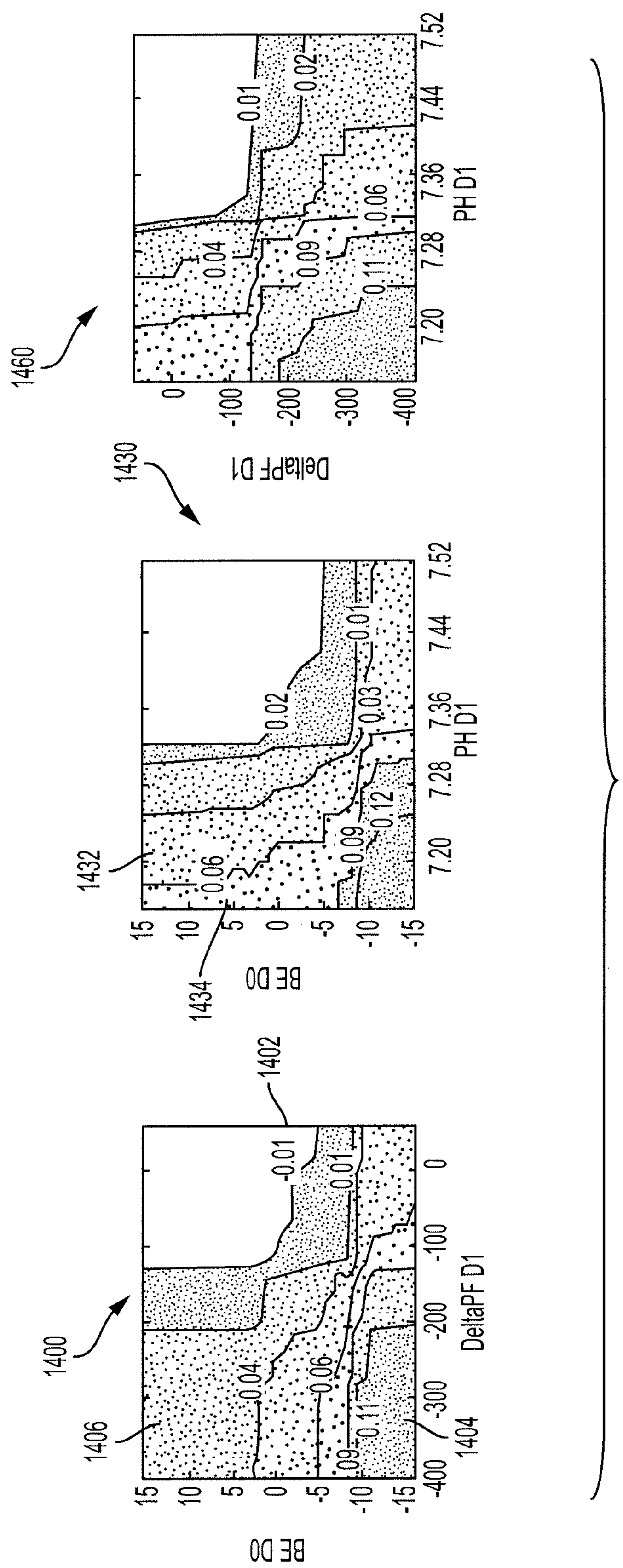
FIG. 14 illustrates multiple pairwise partial dependence plots of top features of an interpretable machine learning model trained to mimic operation of a neural network according to an embodiment of the present invention.

Two-Way Partial Dependence: in practical applications, it may be of greater help to understand the interactions between most important features. One possible way is to generate 2-dimensional partial dependence for important feature pairs. FIG. 14 illustrates multiple plots 1400 demonstrating the two-way dependence scores of the top three features used in the GBT mimic model. From a first plot 1402, it can be seen that the combination of severe metabolic acidosis (low base excess) and relatively large reduction in PF ratio may indicate that the patients are developing multiple organ failures, which leads to mortality (as shown in area 1404). However, a relatively large drop in PF ratio alone, without metabolic acidosis, is not associated with mortality (as shown in area 1406). From a second plot 1430, it can be seen that a low PH value from metabolic acidosis (i.e., with low base excess) may lead to mortality. However, respiratory acidosis itself may not be a negative sign, since if pH is low but not from metabolic acidosis, the outcome is milder (as shown in areas 1432, 1434). A third plot 1460 illustrates that a low pH with falling PF ratio is a negative sign, which likely results from a worsening disease on day 1. But a low pH without much change in oxygenation may not be important in mortality prediction. These findings may be clinically significant and have been corroborated by doctors.

Figure 15:
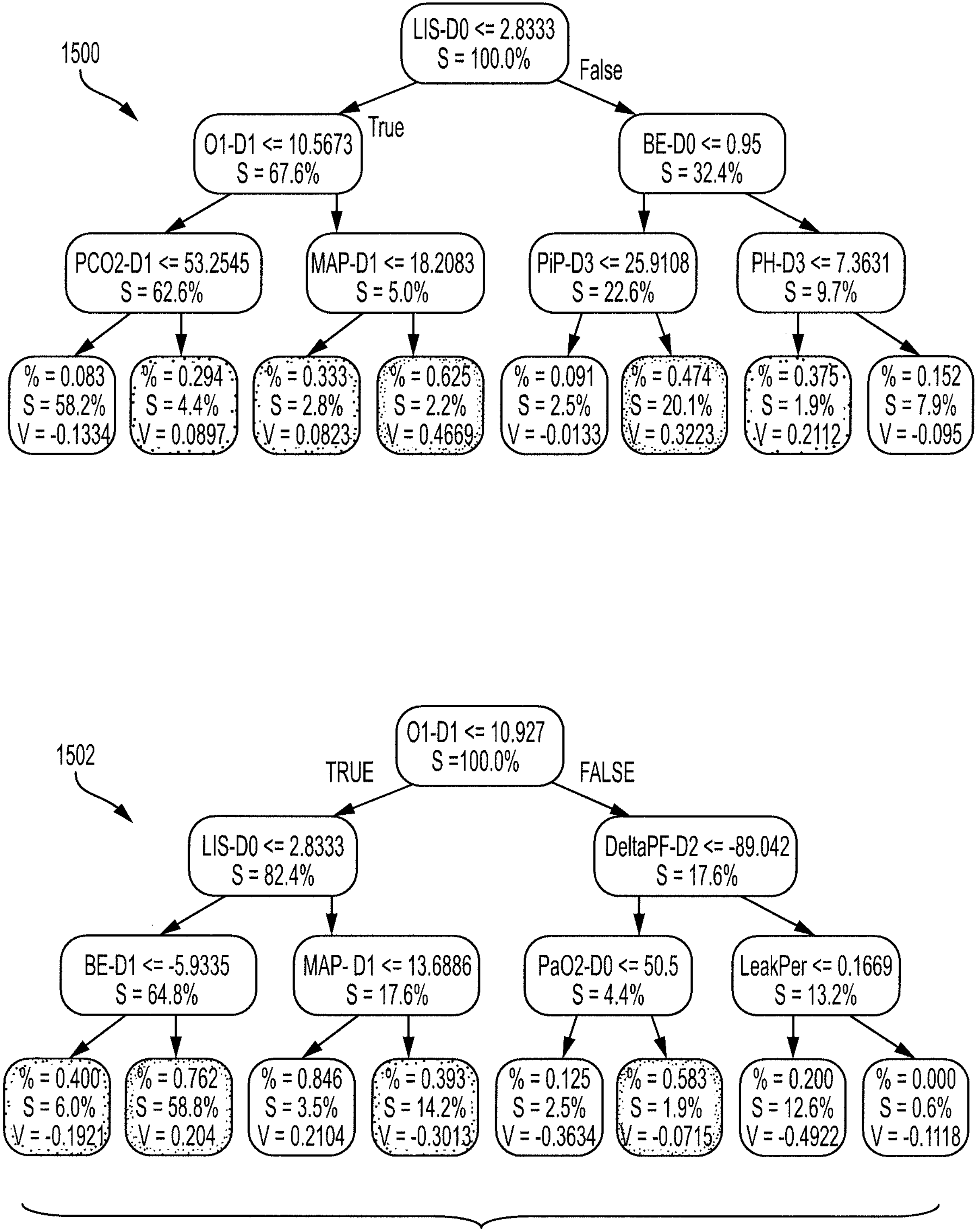
FIG. 15 illustrates two decision trees of a gradient boosting tree trained as an interpretable machine learning model trained to mimic operation of a neural network according to an embodiment of the present invention.

Another way to evaluate the mimic methods is to compare and interpret the trees obtained from our models (such as those output in block 214 of the method 200 of FIG. 2). FIG. 15 illustrates two relatively important decision trees 1500, 1502 (i.e., the trees with the highest coefficient weight in the final prediction function) built by interpretable mimic learning methods for MOR and VFD tasks. Some observations from these trees are as follows: markers of lung injury such as lung injury score (LIS), oxygenation index (OI), and ventilator markers such as Mean Airway Pressure (MAP) and PIP may be the most discriminative features for the mortality task prediction, which has been previously reported. However, the selected trees 1500, 1502 illustrate decision rules with greater granularity than previously possible. For example, it may be studied how the feature values on different admission days can impact the mortality prediction outcome. Similar observations may be made for the VFD task. It may be noticed that the potentially most important tree 1500 includes features, such as OI, LIS, Delta-PF, as top features for VFD task, which again is supported by earlier findings.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method for computational phenotyping, comprising:

training a neural network having a prediction layer using an input including at least one of user provided input corresponding to health metrics or sensor input detected by a sensor and corresponding to the health metrics, and using a target corresponding to a desired output for the input;

determining at least one of soft prediction scores of the prediction layer of the neural network or activations of a highest hidden layer of the neural network corresponding to layer inputs of the highest hidden layer; and training a gradient boosting tree model to mimic the neural network based on the input to the neural network and the at least one of the soft prediction scores of the prediction layer of the neural network or the activations of the highest hidden layer of the neural network.

2. The method of claim 1 further comprising providing a new input to the gradient boosting tree model to predict a new output.

3. The method of claim 1 wherein the neural network further includes at least two hidden layers and training the gradient boosting tree model to mimic the neural network further includes training the gradient boosting tree model using the activations of the highest hidden layer of the at least two hidden layers.

4. The method of claim 3 wherein training the gradient boosting tree model using the activations of the highest hidden layer of the at least two hidden layers further includes:

training a classifier using the activations of the highest hidden layer and the target;

determining classifier soft prediction scores based on the trained classifier; and training the gradient boosting tree model to mimic the neural network based on the input to the neural network and the classifier soft prediction scores.

5. The method of claim 4 wherein the classifier includes logistic regression.

6. The method of claim 1 wherein training the gradient boosting tree model to mimic the neural network further includes training the gradient boosting tree model using the soft prediction scores of the prediction layer of the neural network.

7. The method of claim 1 wherein the neural network includes at least one of:

a feedforward network having multiple nonlinear layers such that a layer output of each nonlinear layer is used as a layer input for each subsequent nonlinear layer;

a stacked autoencoder network that includes encoder networks and decoder networks with tied weights to minimize a squared reconstruction loss to the input; or a long short-term memory network that includes multiple blocks that each determine a cell state and a block output based on a previous cell state, a previous block output, and a current time series input.

8. The method of claim 7 wherein the long short-term memory network further includes a memory prediction layer configured to predict a memory output based on the block output of each of the multiple blocks.

9. The method of claim 1 wherein the gradient boosting tree model includes a plurality of weak learners each including at least one of a classifier or a regression tree, and includes a prediction function that predicts a tree output based on tree inputs and the plurality of weak learners.

* * * * *